United States Patent [19]

Barua et al.

[11] Patent Number: 5,075,340

[45] Date of Patent: Dec. 24, 1991

[54] RETINOIC ACID GLUCURONIDE PREPARATIONS FOR APPLICATION TO THE SKIN

[75] Inventors: Arun B. Barua; Desiree Gunning; James A. Olson, all of Ames, Iowa

[73] Assignee: Iowa State University Research Foundation, Ames, Iowa

[21] Appl. No.: 570,337

[22] Filed: Aug. 21, 1990

Related U.S. Application Data

[63] Continuation-in-part of Ser. No. 355,778, May 22, 1989, abandoned.

[51] Int. Cl.$^5$ .................... A61K 31/07; A61K 31/70
[52] U.S. Cl. .................................. 514/725; 514/25; 514/859
[58] Field of Search .................. 514/725, 859, 25

[56] References Cited

U.S. PATENT DOCUMENTS

| | | | |
|---|---|---|---|
| 3,856,934 | 12/1974 | Kligman | 424/62 |
| 3,906,108 | 9/1975 | Felty | 514/560 |
| 4,457,918 | 7/1984 | Holick et al. | 514/25 |
| 4,473,503 | 9/1984 | Barua et al. | 260/408 |
| 4,565,863 | 1/1986 | Bollag et al. | 536/18.2 |
| 4,603,146 | 7/1986 | Kligman | 514/559 |
| 4,727,088 | 2/1988 | Scott et al. | 514/725 |
| 4,855,463 | 8/1989 | Barua et al. | 549/417 |
| 4,888,342 | 12/1989 | Kligman | 514/419 |

FOREIGN PATENT DOCUMENTS 1335867 10/1973 United Kingdom .

OTHER PUBLICATIONS

Gallup et al., Proc. Soc. Exper. Biol. & Med., 186:269–274 (1987).
Zile et al., Proc. Natl. Acad. Sci. U.S.A., 84:2208–2212 (1987).
Rosa et al., Teratology, 33:355–364 (1986).
Gallup et al., First Mid-America Molecular Biol. Colloquim, p. 35, Oct. 1986.
Barua et al., Amer. J. Clin. Nutr., 43:481–485 (1986).
Takabayashi et al., Chem. Abs., 73, 69834 (1970).
Zile et al. J. Biol. Chem., 257:3537–3543 & 3544–3550 (1982).
Bollenback et al., J. Amer. Chem. Soc. 77:3310–3315 (1955).
Weiss et al., J. Am. Acad. Dermatol., 19:169–175 (1988).
Lippel et al., J. Lipid Research, 9:580–586 (1968).
Barua et al., J. Lipid Research, 26:258–261 (1985).
Barua et al., Biochemica et Biophysica Acta, 757:288–295 (1983).
Ubels et al, Current Eye Research, 4:1049–1057 (1985).
Gunning et al., Abs. 1402, FASEB Annual Meeting, Mar. 1989.

*Primary Examiner*—John W. Rollins
*Attorney, Agent, or Firm*—Tilton, Fallon, Lungmus & Chestnut

[57] ABSTRACT

A method and preparation are described for treating human skin with retinoic acid glucuronide (RAG) in a topical carrier. For treatment of acne or wrinkled skin, RAG can be applied in an effective amount which is nonirritating to the skin. Retinoid dermatitis, an objectionable side effect of topical application of retinoid compounds, can thereby be avoided.

13 Claims, No Drawings

RETINOIC ACID GLUCURONIDE PREPARATIONS FOR APPLICATION TO THE SKIN

GRANT REFERENCES

Research relating to the present invention was supported in part by grants from the United States Government; namely, USDA Grant 87-CRCR-1-2320 and NIH Grants DK32793 and DK39733.

RELATED APPLICATION

This application is a continuation-in-part of co-pending application Ser. No. 07/355,778, filed May 22, 1989, now abandoned.

FIELD OF INVENTION

The field of this invention is the topical application of vitamin A and derivatives thereof for treatment of skin conditions such as acne and skin aging.

BACKGROUND OF INVENTION

Vitamin A and most derivatives thereof having vitamin A activity are water-insoluble, being hydrophobic, lipid-soluble compounds. For example, neither retinoic acid nor retinol are water-soluble. It is known, however, that the glucuronide and glucose derivatives of retinoic acid and retinol are water-soluble. [See, for example, Lippel and Olson, *J. Lipid. Res.* 9:580-586 (1968); Takabayashi, et al., *Chem. Abs.* 73:69834z (1970); Barua, et al., *Amer J. Clin. Nutr.*, 43:481-485 (1986).] Water-soluble glycoside derivatives of vitamin A are described in U.S. Pat. No. 4,457,918. The retinoic acid glucuronide and retinol glucuronide have been tested for effects in vitro on cultures of HL-60 cells (a continuous human myeloid cell line): Zile, et al., *Proc. Nat. Acad. Sci. USA*, 84:2208-2212 1987); and Gallup, et al., First Mid-America Molecular Biol. Colloquium, p. 36, Oct. 1986; and Zile *Biol. & Med.*, 186:269-274 (1987). Under the conditions of the HL-60 system assay, activity similar to retinoic acid and retinol was reported. Both Gallup, et al. and Zile, et al. found that retinoyl β-D-glucuronide (retinoic acid glucuronide) was at least 6-fold less cytotoxic to HL-60 cells than all-trans retinoic acid.

The all-trans form of retinoic acid has been named tretinoin. Cream, gel and liquid preparations containing tretinoin have been approved in the United States for treatment of acne. These preparations are being marketed under the trademark "Retin-A" by the Dermatological Division of Ortho Pharmaceutical Corporation, Raritan, N.J. Presently available strengths of "Retin-A" on a weight percent basis are 0.025% or 0.01% for the gel, 0.1% or 0.05% for the cream, and 0.05% for the liquid. Other potential uses for topical tretinoin have been reported, including treatment of aging skin (Weiss, et al., *J. Amer. Acad. Dermat.* 19:169-175, 1988), and treatment of xerophthalmia and corneal epithelial wounds (Ubels, et al., *Current Eye Research*, 4:1049-1057 1985).

Topical tretinoin is being experimentally tested for treatment of aging skin. It has been found, however, that the patients under treatment may experience local erythema and peeling of the skin, as has been observed in acne treatment. The degree of irritation varies with the strength of the preparation and the frequency of its application, higher concentrations and more frequent application producing a greater number of skin irritation side effects. When such side effects are noted, the treatment can be discontinued for a number of days, a preparation of lower strength used, or the time between applications can be increased. In view of the clinically beneficial results obtained in the treatment of acne and the promising results with respect to improving the condition of aging skin, it would be desirable to utilize a less irritating form of retinoic acid.

Weiss, et al. (1988), cited above, reported a double-blind study confirming earlier published reports that treatment with tretinoin is capable of at least partly reversing structural damage associated with extrinsic aging (photoaging) of the skin. I order to minimize skin irritation, Weiss et al. started treatment with 0.1% tretinoin cream on a daily basis, and then advanced the patients to twice-a-day applications. When a patient was unable to tolerate the 0.1% cream, the patient was switched to a 0.05% cream. Most patients were able to continue with the treatments. However, during the course of their study Weiss, et al. found that "more than 90% of the patients experienced some degree of dermatitis in the tretinoin treated areas" (page 172, col. 1). The areas of the skin found most susceptible to retinoid dermatitis were the sides of the neck, the V-area of the neck and chest, the ventral arms, and the antecubital fossae.

SUMMARY OF INVENTION

This invention relates to topical medicaments for application to the epithelium. In specific embodiments, it relates to topical medicaments for application to the skin for treatment of acne and/or skin aging. The topical medicaments of this invention use a specific water-soluble vitamin A derivative in admixture with spreadable topical carriers, such as gels, creams, liquid preparations such as lotions.

The active therapeutic agent for use in the medicaments and treating methods of this invention is retinoic acid glucuronide. This compound is preferably in the all-trans form, but it may also be used in the 13-cis form. The topical medicaments of this invention preferably utilize carriers which contain an aqueous or polar solvent phase so that the water-soluble vitamin A derivatives can be dissolved therein.

Unlike the retinoic acid preparations currently in commercial and clinical use, the preparations of this invention are not irritating to the skin. Not only does the glucuronide moiety provide water-solubility, but it also appreciably reduces side effects which can result in skin redness, scaling, and the like. Since the preparations of this invention are not irritating to the skin, they can be applied to the skin at higher concentrations, and/or more frequent applications can be used. Either procedure ca increase the effectiveness of treatments for acne or skin aging.

DETAILED DESCRIPTION

The water-soluble vitamin A derivatives used in the preparations and methods of this invention are not available commercially, but they can be prepared from commercially available starting materials. These materials include retinoic acid and retinyl acetate, which can be obtained from commercial sources in all-trans or 13-cis forms, for example, from Sigma Chemical Co., St. Louis, Mo. D-glucuronic acid is also available commercially, for example, from Aldrich Chemical Co., Milwaukee, Wis.

Retinoyl fluoride is a useful intermediate for preparing retinoic acid glucuronide also called retinoyl β-glucuronide. A method for preparing all-trans or 13-cis retinoyl fluoride is described in Barua and Olson, *Biochimica. et Biophysica Acta*, 757:288–299 (1983); and U.S. Pat. No. 4,473,503. A two-step process for preparing retinoic acid glucuronide from retinoyl fluoride is described in Barua and Olson, *J. Lipid. Res.*, 26:258–261 (1985). Retinoyl fluoride is first reacted with 6,3-glucuronolactone to produce 6,3-lactone of retinoyl glucuronic acid, which is then hydrolyzed with dilute alkali to give the retinoyl β-glucuronide. A one-step process for this synthesis is described in U.S. Pat. No. 4,855,463. The reaction is carried out in an acetone-water mixture proportioned so that both the water-insoluble retinoyl fluoride and the water-soluble glucuronic acid are maintained in solution.

The preparations of this invention can be formulated as ointments or lotions. The preparations preferably contain a polar or aqueous phase in which the active agent is dissolved. For example, aqueous gels can be used as an ointment base, and liquid preparations can be formulated as aqueous solutions, or with a polar solvent such as glycerol. Alternatively, however, an ointment can be formed from a lipid-base cream. The vitamin A compounds are soluble in polar organic solvents, such as glycerol, and can be formulated therein. Glycerol solutions of the compounds can be combined with gels, creams, or liquid preparations.

Suitable water-soluble ointment bases include polyethylene glycol. Emollients may be included and also preservatives, such as the parabens. More complex topical carrier formulations can also be used. For example, a gel vehicle may consist of butylated hydroxytoluene, hydroxypropyl cellulose, and ethanol. A cream vehicle may consist of a mixture of stearic acid, isopropyl myristate, polyoxylstearate, stearyl alcohol, xanthan gum, sorbic acid, butylated hydroxytoluene, and water. A liquid vehicle may be composed of a mixture of polyethylene glycol, butylated hydroxytoluene, and ethanol. A topical vehicle for tretinoin and isotretinoin is described in U.S. Pat. No. 4,727,088. This vehicle, which contains long chain fatty alcohols and a volatile silicone, can be used with the therapeutic agent of this invention.

Retinoic acid glucuronide ca be combined with the topical carrier (ointment or liquid) in a wider range of strengths than has heretofore been available for retinoic acid preparations. For example, the preparations may be formulated to contain from 0.02 to 0.5 weight percent of the active agent. On the basis of present information, it is believed that the most useful formulations will contain from 0.05 to 0.35% by weight of retinoic acid glucuronide. To maximize therapeutic effect, preparations may need to contain more than 0.15% of the active agent, such as 0.2% up to 0.5% by weight.

It will be understood that the active agent should be homogeneously dispersed in the topical preparations, such as by dissolving in the aqueous phase or by thorough mixing with the vehicle if it does not contain an aqueous or polar phase. For example, a finely divided powder of retinoic acid glucuronide ca be dispersed in an oil-based vehicle such as petrolatum.

The preparations and method of this invention are further illustrated by the following examples.

EXAMPLES I

Synthesis of Retinoyl β-Glucuronide (Retinoic Acid Glucuronide)

Retinoyl fluoride (2.4 g, 7.9 mmol) was dissolved in 200 ml of acetone. D-glucuronic acid (6 g, 31 mmol) dissolved in 50 ml of water and sodium bicarbonate (970 mg) dissolved in 50 ml of water were added to the retinoyl fluoride solution. The mixture wa stirred at room temperature for 20–24 hrs. The solution was neutralized with 1N HCl, diluted with water, and the product was extracted with ethyl acetate. The extract was washed with water, dried over anhydrous sodium sulfate and then evaporated to dryness in a rotary evaporator. The residue was dissolved in 2–3 ml of diethyl ether and transferred to a silica gel (for dry column chromatography, wet packed with hexane) column. The column was developed with hexane containing diethyl ether (5–50%) to remove retinoic acid and other products. The major yellow band containing retinoyl glucuronide was next eluted with a mixture of $CH_2Cl_2/CH_3OH$ (1:1). The solvent was evaporated to dryness to give solid retinoyl β-glucuronide (2.3 g, 60%). This preparation consisted mainly of the all-trans isomer, and can be used as such.

Analytically pure retinoyl β-glucuronide was obtained by HPLC of the above preparation on a Whatman ODS-3 column (M9, 50 cm) using methanol/water (7:3) containing 10 mM ammonium acetate at a flow rate of 3 ml/min. Retinoyl β-glucuronide ($t_R=48.7$ min) separated from traces of isomers or anomers ($t_R=46.4$ min). The eluate carrying retinoyl β-glucuronide was diluted with water, made just acidic with 0.11N HCl and the product was extracted with ethyl acetate. The extract was washed with water, dried over anhydrous sodium sulfate and then evaporated to dryness. The residue was dissolved in a small volume of diethyl ether and all-trans retinoyl β-glucuronide was precipitated with hexane. The solid was separated and dried. All-trans retinoyl β-glucuronide: m.p. 142°–143° C. (darkens at 125° C.); $UV_{max}360$ nm (1% $E_{1cm}=1065$) in methanol and 365 nm in water. The $^1$H-NMR, IR and Mass spectra and C, H analysis results were consistent with the structure. The compound is soluble in water. Incubation of retinoyl β-glucuronide with β-glucuronidase (from *E. coli*) in phosphate buffer (pH 6.8) for 0.5–2 hrs generated retinoic acid.

EXAMPLE II

Preparation of Retinoic Acid Glucuronide Cream

Fifty mg of finely powdered all-trans retinoic acid glucuronide (retinoyl β-glucuronide) was dissolved in 2 g of glycerol by agitating the mixture for several minutes. A commercial lotion (Nivea) (48 g) was added to the solution to bring the concentration of the retinoid to 0.1%. The mixture was stirred well and stored protected from light and heat. Nivea moisturizing lotion is manufactured by Beiersdorf, Inc., Norwalk, Conn.), and is composed of water, mineral oil, glycerin, isopropyl palmitate, glyceryl stearate, ceteryl alcohol, isopropyl myristate, fragrance, acrylamide/sodium acrylate copolymer, lanolin alcohol, simethicon, methylchloroisothiazolinone and methylisothiazolinone.

Another preparation was made in the same way adding 125 mg of the retinoid to 3 g of glycerol and 47 g of the Nivea lotion to give a concentration of 0.25%.

For comparison a retinoic acid cream was prepared as follows: 50 mg of solid all-trans retinoic acid was dissolved in glycerol (2 g) and mixed with 48 g of Nivea cream to give a concentration of 0.1%.

EXAMPLE III

Preparation of Retinoic Acid Glucuronide Lotion

Fifty mg of finely powdered retinoic acid glucuronide was dissolved in 10 g of glycerol by agitating for several minutes. The solution was diluted with 40 ml of water to give a 0.1% lotion of retinoid glucuronide.

EXAMPLE IV

Treatment of Face for Acne

A female volunteer with facial acne applied the 0.1% retinoic acid glucuronide preparation of Example II on her right face, and 0.1% retinoic acid cream of Example II on her left face every night before going to bed.

Within two weeks, the left side (retinoic acid treatment) became tender and red, and peeling of skin occurred. Facial washing and application of make-up became extremely painful. The burning and degree of discomfort forced her to discontinue the treatment with retinoic acid.

The right side of the face (glucuronide treatment) did not show any sign of the above problems, although at the beginning the eyelids were highly sensitive to the cream, which sensitivity disappeared within a few days. After a month of the glucuronide treatment, the face was clear and smooth with no visible blemishes.

Application of the 0.25% glucuronide preparation of Example V on the volunteer's face did not result in any burning or peeling or other discomfort.

Another female volunteer with facial acne is being treated with the 0.1% glucuronide preparation of Example V. A marked degree of progress has been observed in three weeks. No burning or peeling of skin or other discomforts have been noted.

EXAMPLE V

Treatment for Wrinkles

A male volunteer with slight wrinkles around his eyes applied 0.1% lotion of the retinoic acid glucuronide lotion of Example VI on his face every night for over six months. The severity of wrinkles diminished considerably. No side effects were observed or reported.

EXAMPLE VI

Treatment for Cracked Lips

During the winter and dry season, when his lips were cracked, a male volunteer applied the 0.1% retinoic acid glucuronide lotion of Example VI on his lips before going to bed. The cracks disappeared with a few days of application.

EXAMPLE VII

Clinical Trial of Retinoic Acid Glucuronide

This study was carried out under the supervision of a local dermatologist using human acne volunteers.

A cream containing all-trans retinoic acid glucuronide (RAG) was prepared (0.16 wt. % RAG is the molar equivalent of 0.1% retinoic acid) as follows:

All ingredients, except retinoic acid glucuronide, are available commercially (ICI-Atlas, Atlas Chemical Division, Wilmington, Del.). The ingredients are of cosmetic grade.

| Part I | |
|---|---|
| Stearic acid | 5% (weight/weight) |
| Isopropyl myristate | 2% |
| Arlacel 165 | 5% |
| Butylated hydroxytoluene | 0.02% |
| Part II | |
| Sorbo (sorbitol) | 20% |
| Retinoic acid glucuronide | 0.16–0.32% |
| Water | 67.66–67.82% |

To prepare the cream, retinoic acid glucuronide was dissolved in the Sorbo and water mixture by stirring, and then heated to 72° C. (Part II). Ingredients in Part I are mixed and heated to 70° C. Part I and Part II are mixed and stirred vigorously until setting to a cream or heavy lotion. The cream is then poured into tubes and sealed.

The cream was transferred to tubes which were color coded (blue). "Retin A" cream (RA) (Ortho Pharmaceutical) (0.1% retinoic acid) was purchased from a pharmacy and transferred to tubes which were color coded (red).

Acne patients received the base cream (without the active ingredient, RAG) for 2 weeks. This was done in order to ascertain that the base cream would not cause adverse reaction (redness, irritation, etc.) to the skin. After 2 weeks, in a double blind study, one group of 10 volunteers were supplied with the blue tubes (containing RAG), and the other group of 5 volunteers received the red tubes (containing RA). All the volunteers applied the cream once every night before going to bed. After one month, when it was found that the volunteers applying cream from the blue tube (0.16% RAG) did not show any side effects, the concentration of RAG in the base cream was raised for all patients to 0.24% (green tube) and finally to 0.32% (yellow-green tube) after another month.

The supervising dermatologist kept records of counts of papulo-pustules (PP), cysts, comedones and pigmentation at the beginning of the study, and during subsequent visits during the next 7 months. The dermatologist also recorded any changes in skin condition. Photographs of the treated skin were taken at periodic intervals during the trial, and each subject was asked to judge the effectiveness of the treatment.

Results

The results of the 7-month trial are summarized in Tables A and B. All patients receiving either RAG or RA showed improvements of their skin condition ranging from 30–100%. Significantly, however, all patients receiving Retin A (RA) showed skin irritation side effects. None of the patients receiving RAG showed any skin irritation effects.

TABLE A

| | Clinical Trial of Retinoic Acid Glucuronide (RAG) on Human Acne Volunteers | | | | | | | | |
|---|---|---|---|---|---|---|---|---|---|
| | Initial Counts | | Final Counts | | Total Counts | | | Physician | |
| Volunteers[a] | PP & Cysts | Comedones | PP & Cysts | Comedones | Before | After | % Improvement | Evaluation | Irritation |
| 1-SG | 7 | 29 | 2 | 11 | 36 | 13 | 64 | Good | none |

TABLE A-continued

Clinical Trial of Retinoic Acid Glucuronide (RAG) on Human Acne Volunteers

| Volunteers[a] | Initial Counts PP & Cysts | Initial Counts Comedones | Final Counts PP & Cysts | Final Counts Comedones | Total Counts Before | Total Counts After | % Improvement | Physician Evaluation | Irritation |
|---|---|---|---|---|---|---|---|---|---|
| 2-JCY | 6 | 8 | 2 | 2 | 14 | 4 | 71 | Good to Excellent | none |
| 3-RO | 12 | 43 | 0 | 4 | 55 | 4 | 93 | Excellent | none |
| 4-RR | 7 | 11 | 0 | 0 | 18 | 0 | 100 | Excellent | none |
| 5-KT | 5 | 16 | 6 | 8 | 21 | 14 | 33 | Fair | none |
| 6-PS | 24 | 25 | 7 | 4 | 49 | 11 | 78 | Good to Excellent | none |
| 7-TM | 10 | 6 | 4 | 5 | 16 | 9 | 44 | Good | none |
| 8-JF | 6 | 9 | 0 | 0 | 15 | 0 | 100 | Excellent | none |
| 9-KH | 23 | 15 | 0 | 3[c] | 38 | 3 | 92 | Good to Excellent | none |
| 10-MB (R side)[b] | 15 | 29 | 5 | 17 | 44 | 22 | 51 | RAG better than 0.025 Retin-A | none on right side |
| TOTAL | | | | | 306 | 80 | 74% | | |
| MEAN | | | | | 30.6 | 8 | | | |

[a]Nine volunteers used the RAG cream, applied to both sides of the face.
[b]Volunteer MB used RAG cream only on the right side of the face.
[c]Volunteer JF discontinued before the study was completed.

TABLE B

Comparative Clinical Trial of Retin-A on Human Acne Volunteers

| Volunteers[a] | Initial Counts PP & Cysts | Initial Counts Comedones | Final Counts PP & Cysts | Final Counts Comedones | Total Counts Before | Total Counts After | % Improvement | Physician Evaluation | Irritation |
|---|---|---|---|---|---|---|---|---|---|
| 11-JG | 25 | 10 | 4 | 6 | 35 | 10 | 71 | Very Good | all patients reported the following: redness, burning, peeling, itching, extreme dryness observed on left side |
| 12-MC | 23 | 13 | 13 | 9 | 36 | 22 | 39 | Mild to Fair | |
| 13-KS | 32 | 8 | 6 | 2 | 40 | 8 | 80 | Excellent | |
| 14-JS | 17 | 83 | 6 | 2 | 100 | 8 | 92 | Excellent | |
| 10-MB (L side)[b] | 10 | 16 | 9 | 9 | 26 | 18 | 30 | Not as good as RAG (R side) | |
| TOTAL | | | | | 237 | 66 | 72% | | |
| MEAN | | | | | 47.4 | 13.2 | | | |

[a]Four volunteers used the Retin-A applied to both side of the face.
[b]Volunteer MB used Retin-A only on the left side of the face.

We claim:

1. The method of treating human skin with a preparation in which a retinoid compound is applied to the skin in a topical carrier, wherein the improvement comprising utilizing in said preparation as said retinoid compound an effective amount of retinoic acid glucuronide (RAG) which effective amount is non-irritating to the skin.

2. The method of treating acne on human skin while avoiding the side effect of retinoid dermatitis, comprising applying a topical medicament to the acne afflicted area of a human patient's skin, said topical medicament comprising an effective amount of retinoic acid glucuronide (RAG) in admixture with an emollient carrier having a liquid phase, said RAG being in all-trans or 13-cis form and being dissolved in the liquid phase of said carrier.

3. The method of claim 2 in which the liquid phase is an aqueous phase.

4. The method of claims 1, 2 or 3 in which said RAG is in all-trans form and is present in an amount from about 0.05 to 0.35 weight percent.

5. A method of treating aging human skin with a retinoid compound while avoiding the side effect of retinoid dermatitis, comprising applying to wrinkled skin areas a topical medicament comprising an effective amount of retinoic acid glucuronide (RAG) in admixture with an emollient carrier having a liquid phase, said RAG being all-trans or 13-cis form and being dissolved in said liquid phase.

6. The method of claim 5 in which said liquid phase is an aqueous phase.

7. The method of claim 5 or 6 in which said RAG is in all-trans form and is present in an amount from about 0.05 to 0.35 weight percent.

8. The method of claims 2 or 5 in which said carrier is an ointment.

9. The method of claims 2 or 5 in which said carrier is a lotion.

10. A non-irritating topical medicament for treatment of human skin, comprising a composition in the form of an ointment or lotion containing an effective amount of retinoic acid glucuronide (RAG) in an emollient carrier, said carrier having a liquid phase in which said RAG is dissolved and said RAG being in all-trans or 13-cis form.

11. The topical medicament of claim 10 in which said RAG is present in said composition in an amount of from about 0.05 to 0.35 weight percent.

12. The topical medicament of claim 10 in which said liquid phase is an aqueous phase.

13. The topical medicament of claims 10, 11 or 12 in which said RAD is in all-trans form.

* * * * *

UNITED STATES PATENT AND TRADEMARK OFFICE
CERTIFICATE OF CORRECTION

PATENT NO. : 5,075,340

DATED : December 24, 1991

INVENTOR(S) : Barua et al.

It is certified that error appears in the above-identified patent and that said Letters Patent is hereby corrected as shown below:

```
Column 2, line 14, delete "I" and insert --In--.
Column 2, line 55, delete "ca" and insert --can--.

Column 3, line 48, delete "ca" and insert --can--.
Column 3, line 65, delete "ca" and insert --can--.

Column 4, line 9, delete "wa" and insert --was--.
Column 4, line 35, delete "0.11" and insert --0.1--.

Column 8, line 66, delete "RAD" and insert --RAG--.
```

Signed and Sealed this

Fourth Day of May, 1993

Attest:

MICHAEL K. KIRK

Attesting Officer

Acting Commissioner of Patents and Trademarks